US00PP30483P3

(12) United States Plant Patent
Suphachadiwong

(10) Patent No.: US PP30,483 P3
(45) Date of Patent: May 7, 2019

(54) ***VANDA* PLANT NAMED 'SPCDW1702'**

(50) Latin Name: ***Vanda* spp. Jones ex R. Br.**
Varietal Denomination: SPCDW1702

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/932,467

(22) Filed: Mar. 1, 2018

(65) Prior Publication Data

US 2018/0255687 P1 Sep. 6, 2018

(30) Foreign Application Priority Data

Mar. 1, 2017 (QZ) ..... PBR 2017/0651

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — Samuel R. McCoy, Jr.

(57) ABSTRACT

A new and distinct variety of *Vanda* plant named 'SPCDW1702' which is characterized by large flowers carried slightly above the foliage, flowers which generally appear to be bicolored with the upper half of the flower colored violet and the lower half generally colored dark purple, a labellum with a deep purple central lobe and light purple lateral lobes which are radially striped yellow-green, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1702'.

CROSS REFERENCE TO RELATED APPLICATIONS

This application claims priority to the Community Plant Variety Rights application number 2017/0651, filed Mar. 1, 2017, which is herein incorporated by reference.

BACKGROUND OF THE INVENTION

Parentage: The *Vanda* variety 'SPCDW1702' is the result of a planned breeding program. The new variety originated as a seedling from the crossing of *Vanda* 'K1BL' (not patented), the seed parent, with *Vanda* 'V152N1' (not patented), the pollen parent. Both parents were developed by, and are owned by, the inventor and were never commercially released. The crossing was made by the inventor in his research greenhouse in Bangphra, Thailand in December of 2005.

The new variety was first selected in May of 2010, in a research greenhouse in Bangphra, Thailand belonging to the inventor. After identifying the new variety as a potentially interesting selection, the inventor continued confidential testing and propagation of 'SPCDW1702', assessing stability of the unique characteristics of this variety.

Asexual Reproduction: Asexual reproduction of the new cultivar 'SPCDW1702', by way of mericloning, was first initiated in March of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1702' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1702'. These characteristics in combination distinguish 'SPCDW1702' as a new and distinct *Vanda* cultivar:

1. *Vanda* 'SPCDW1702' exhibits large flowers carried slightly above the foliage; and
2. *Vanda* 'SPCDW1702' exhibits flowers which appear to be bicolored, with the upper half of the flower generally colored violet, and the lower half generally colored dark purple; and
3. *Vanda* 'SPCDW1702' exhibits violet lateral flower petals and a violet dorsal sepal, all of which are dotted and blotched with dark purple; and 4. *Vanda* 'SPCDW1702' exhibits violet lateral sepals which are heavily blotched and veined dark purple, giving the sepals a generally dark purple appearance; and
5. *Vanda* 'SPCDW1702' exhibits a labellum with a deep purple central lobe, and light purple lateral lobes which are radially striped yellow-green.

BOTANICAL DESCRIPTION OF THE PLANT

Figure 1:
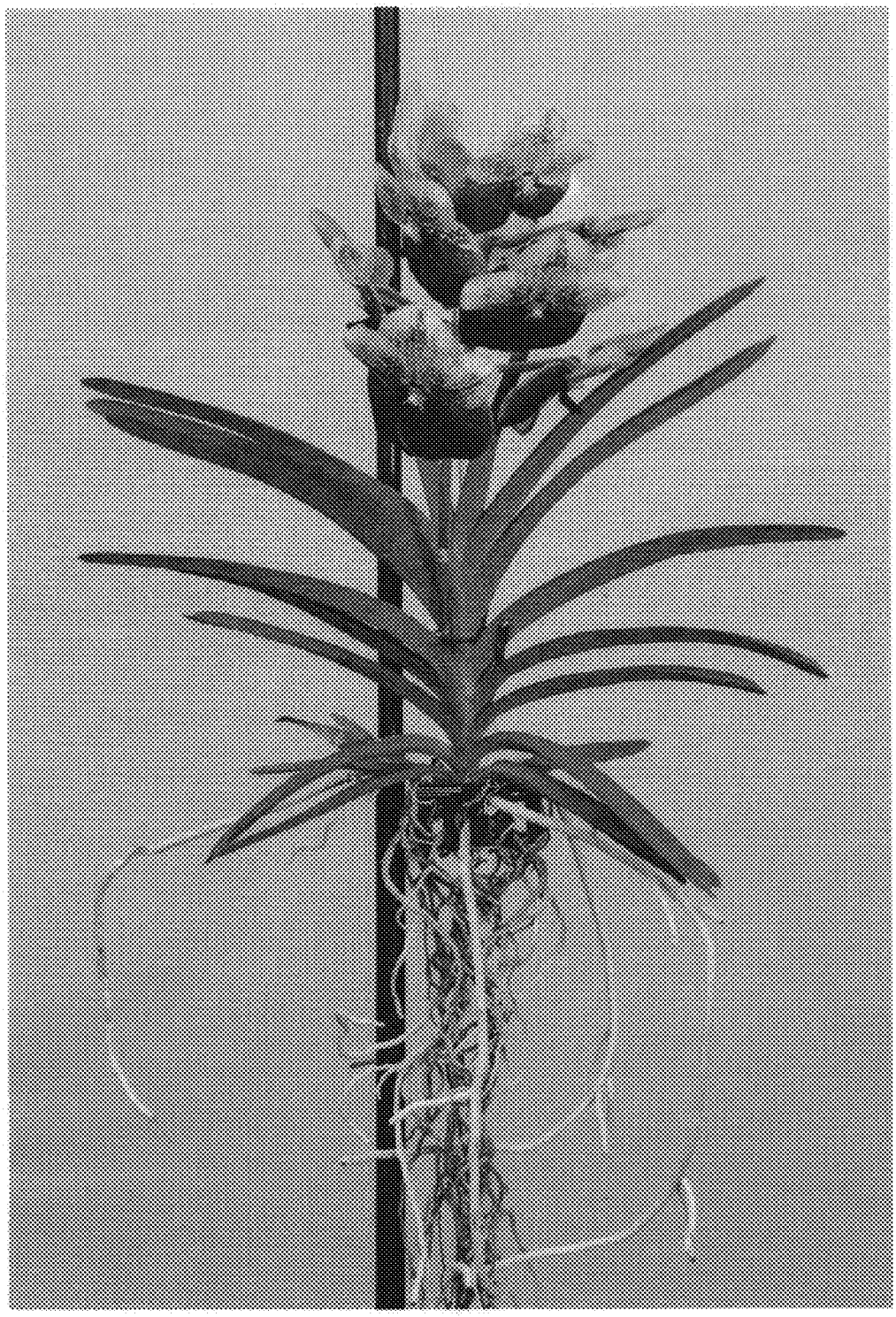
FIG. 1 illustrates, as nearly true as it is reasonably possible to make the same in color photographs of this type, an exemplary plant of 'SPCDW1702' grown in a commercial greenhouse in Honselersdijk, the Netherlands. This plant is approximately 6 years old from the time of mericloning, shown planted in an 8 by 2 cm container.
Figure 2:
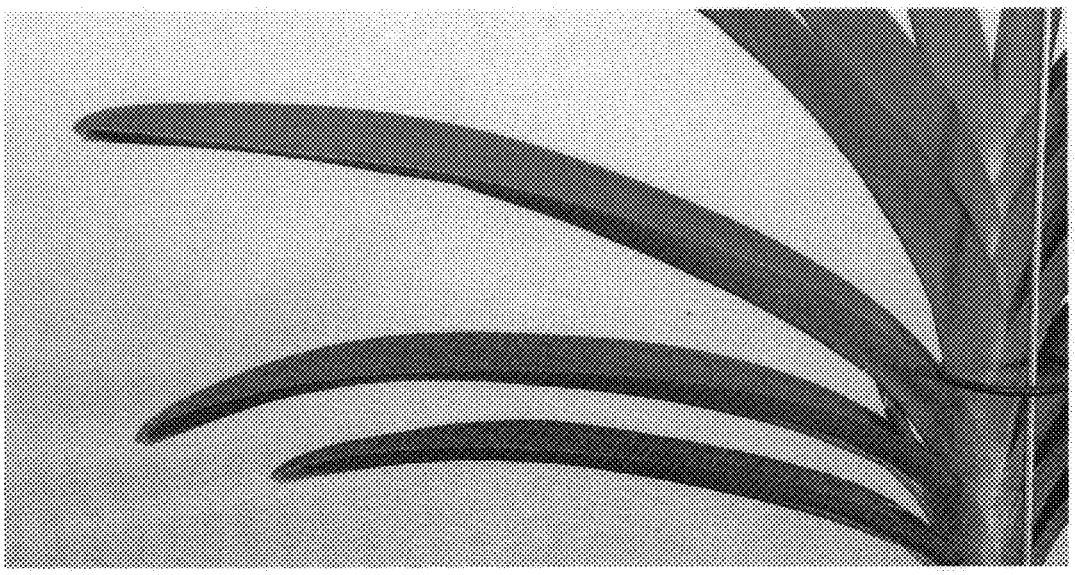
FIG. 2 illustrates, as nearly true as it is reasonably possible to make the same in color photographs of this type, the typical foliage of 'SPCDW1702'.
Figure 3:
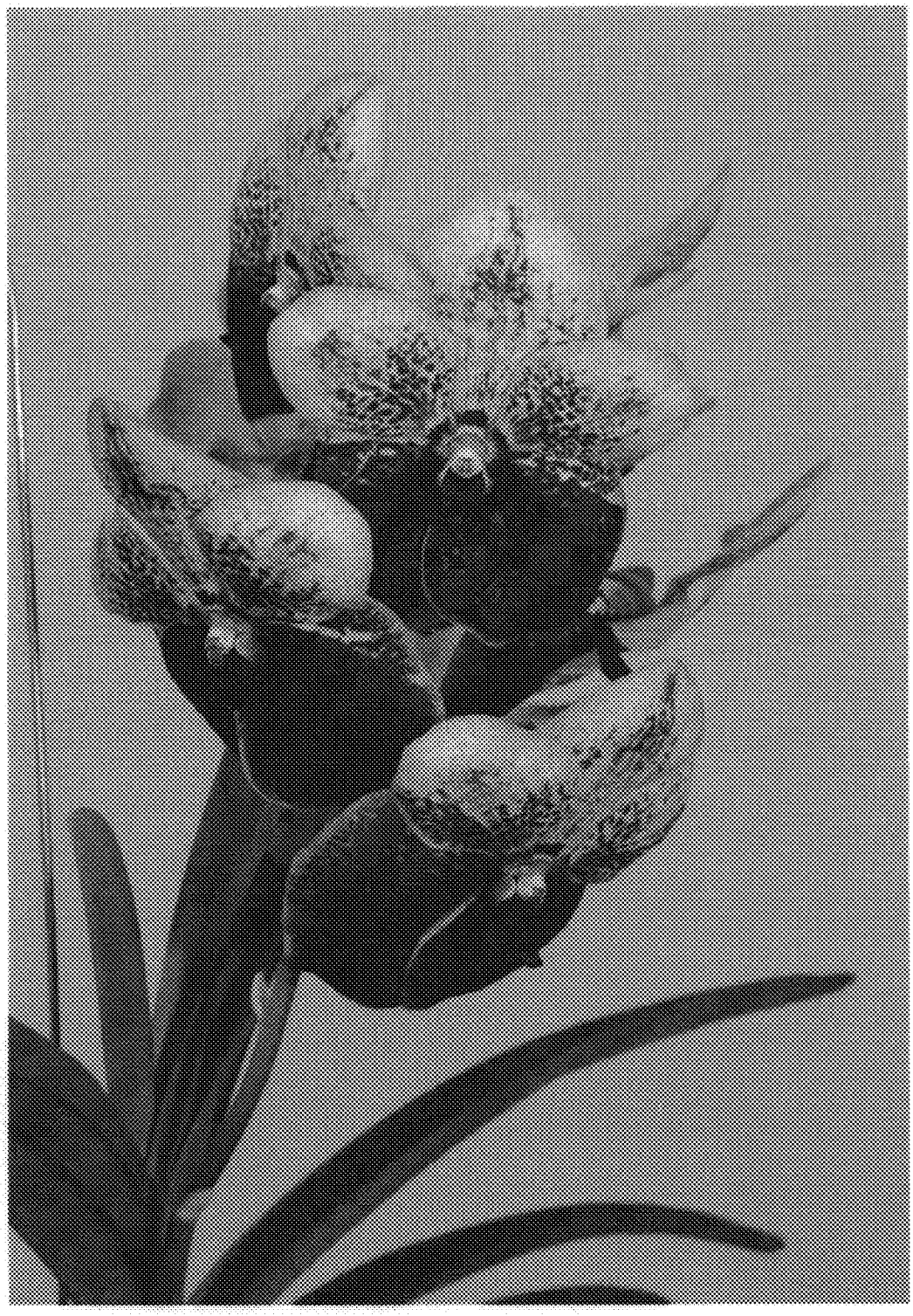
FIG. 3 illustrates, as nearly true as it is reasonably possible to make the same in color photographs of this type, the typical inflorescence of 'SPCDW1702'.
Figure 4:
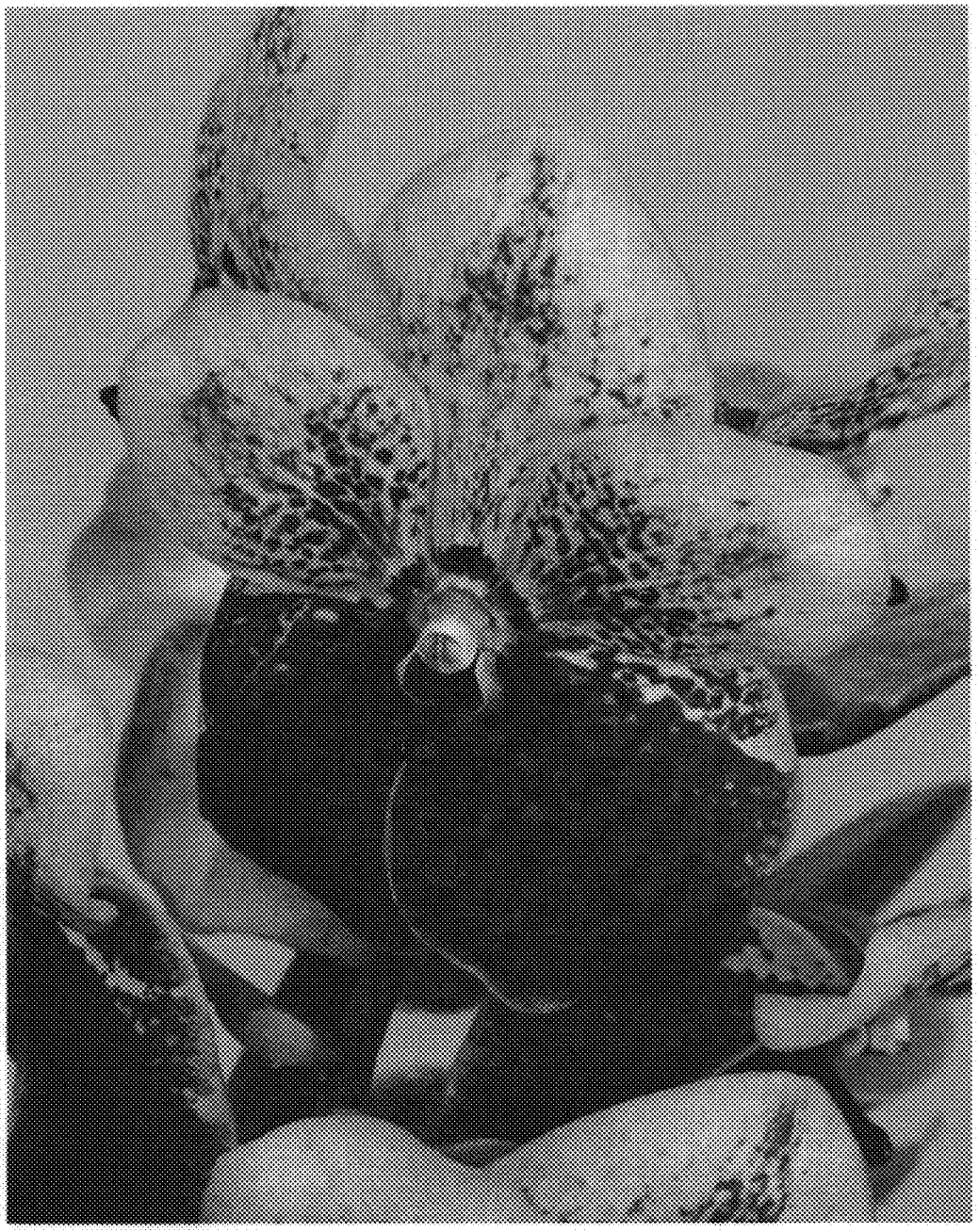
FIG. 4 illustrates, as nearly true as it is reasonably possible to make the same in color photographs of this type, the typical flower of 'SPCDW1702'.

The following observations and measurements made in January of 2018 describe averages from a sample set of six specimens of six year-old 'SPCDW1702' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1702' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1702' and comparisons with the parents and most similar commercial varieties of *Vanda* are provided below.

Plant description:

*Growth habit.*—Perennial; monopodial, upright. Single monopodial leafy stem, with flowers carried slightly above the leaf plane; inflorescences growing from the leaf axils.

*Average height from base (plant grown in hanging basket, so no soil line present) to foliar plane.*—31.0 cm.

*Average height from base (plant grown in hanging basket, so no soil line present) to top of floral plane.*—40.1 cm.

*Plant spread.*—Average of 35.9 cm.

*Appropriate container size.*—8 cm by 2 cm rectangular hanging basket.

*Growth rate.*—Moderate.

*Plant vigor.*—Moderate.

*Propagation type.*—Meristematic tissue culture propagation using the base of the leaves.

*Propagation details.*—The time needed from the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility.*—Plants have not been observed to be susceptible or resistant to pathogens and pests common to *Vanda*.

*Environmental tolerances.*—Adapt to, at least, USDA Zones 11 and 12 and temperatures as high as 40 degrees Celsius; high tolerance to rain; moderate to high tolerance to wind.

Root system:

*General.*—Moderately dense rooting; with aerial roots only.

*Dimensions, mature roots.*—54.1 cm long with a diameter of 0.5 cm, on average.

*Texture.*—Very fleshy; non-fibrous.

*Color.*—Greyed-green, nearest to RHS 192C; root apex is yellow-green, RHS 148A.

Stem:

*Branching habit.*—Monopodial; no lateral branches present.

*Number of primary (main) stems per plant.*—One.

*Number of secondary (lateral) branches per plant.*—None.

*Appearance and shape.*—Circular, formed by the leaf sheaths.

*Length.*—12.4 cm.

*Diameter.*—1.0 cm.

*Internode length.*—0.8 cm.

*Luster.*—Matte.

*Aspect, main stem.*—Near vertical.

*Strength.*—Very strong.

*Color, juvenile.*—Yellow-green, nearest to RHS 145D.

*Color, mature.*—Yellow-green, nearest to RHS 150D.

*Color at internodes.*—Yellow-green, nearest to RHS 150D.

*Pubescence.*—Glabrous.

Foliage:

*Arrangement.*—Distichous.

*Dimensions.*—26.3 cm long, excluding the sheath, and 2.7 cm wide.

*Shape of blade.*—Ligulate; moderately to strongly carinate.

*Aspect.*—Slightly to moderately curved.

*Apex.*—Unequal praemorse.

*Base.*—Sheathing.

*Sheath dimensions.*—3.9 cm long and 1.3 cm wide, on average.

*Sheath color.*—Yellow-green, nearest to in between RHS 145B and 145C.

*Margin.*—Entire.

*Pubescence, texture and luster of adaxial surface.*—Glabrous, smooth, and matte.

*Pubescence, texture and luster of abaxial surface.*—Glabrous, smooth, and matte.

*Color.*—Juvenile foliage, adaxial surface — Yellow-green, nearest to RHS 144A. Juvenile foliage, abaxial surface — Yellow-green, nearest to RHS 144A, and darker towards the margins, nearest to RHS 143A. Mature foliage, adaxial surface — Green, nearest to RHS NN137B. Mature foliage, abaxial surface — Yellow-green, nearest to RHS 146B.

*Venation.*—Parallel.

*Venation color, adaxial surface.*—Green, nearest to RHS NN137B.

*Venation color, abaxial surface.*—Yellow-green, nearest to RHS 144B.

*Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 9.

*Flowers per plant.*—8 open flowers and 1 flower buds.

*Inflorescence height.*—Approximately 21.0 cm (measured from base of lowest flower to top of upper flower).

*Inflorescence diameter.*—Approximately 19.3 cm.

*Peduncle.*—Dimensions — Approximately 31.1 cm long and 0.45 cm wide. Aspect — Generally at a 15 degree angle to lateral branch axis. Strength — Moderately strong. Texture and luster — Glabrous and matte. Color — Yellow-green, nearest to RHS 144A.

Bud:

*Length.*—Average of 1.4 cm.

*Diameter.*—Average horizontal diameter is 1.5 cm; the vertical diameter is 1.6 cm.

*Shape.*—Cubic, with a deltoid apex which is pointed downward.

*Pubescence, texture and luster.*—Glabrous, smooth and slightly glossy.

*Color.*—Yellow-green, nearest to RHS 146D, and lightly suffused with purple at the apex, nearest to RHS N77B; base is yellow-green, nearest to RHS 145B.

Flower:

*Flower type.*—Zygomorphic (orchidaceous), typical shape for the genus *Vanda*.

*Flowering habit.*—Moderately free flowering.

*Shape.*—Zygomorphic, single; consisting of three sepals and three petals, one of which is transformed into a labellum; the two lateral petals slightly overlap the lateral sepals and moderately overlap the dorsal sepal; lateral sepals overlap one another.

*Attitude.*—Flowers are outward-facing to slightly nodding.

*Vertical height.*—Approximately 11.8 cm.

*Diameter.*—Approximately 10.3 cm.

*Depth.*—Approximately 3.8 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.2 cm. Width — Approximately 4.0 cm. Shape — Broad obovate. Apex — Obtuse. Base — Cuneate. Margin — Entire; not undulated to lightly undulated. Pubescence, texture and luster of upper surface — Glabrous, velvety and matte. Pubescence, texture and luster of lower surface — Glabrous, velvety and matte. Color when opening, upper surface — Distal two-thirds portion of the petal is purple-violet, nearest to RHS N82D, and finely dotted violet, nearest to RHS 83B; the proximal one-third portion of the petal is white, nearest to RHS NN155D and dotted purple, nearest to RHS 79A; base of the petal is greyed-purple, nearest to in between RHS N186B and N186C. Color when opening, lower surface — Purple-violet, nearest to RHS N82D, and fading white towards the base, nearest to RHS 155C; sparsely covered with fine violet dots at the base, nearest the RHS 83A. Color when fully opened, upper surface — Distal two-thirds portion of the petal is violet, nearest to RHS N87D but slightly lighter, and finely dotted purple, nearest to RHS N79B; the proximal one-third portion of the petal is in between violet and greyed-green, nearest to RHS 84D and 196C, and dotted purple, nearest to RHS 79A; base of the petal is greyed-purple, nearest to RHS N186A. Color when fully opened, lower surface — In between purple-violet and violet, nearest to RHS N82D and 85A; suffused with greyed-white towards the base, nearest to RHS 156D. Fading, upper surface — Not fading. Fading, lower surface — Not fading. Venation — Densely reticulate. Venation color, fully opened, upper surface — Distal two-thirds portion of the petal is violet, nearest to RHS N87D but slightly lighter, and finely dotted purple, nearest to RHS N79B; the proximal one-third portion of the petal is in between violet and greyed-green, nearest to RHS 84D and 196C, and dotted purple, nearest to RHS 79A; base of the petal is greyed-purple, nearest to RHS N186A. Venation color, fully opened, lower surface — In between purple-violet and violet, nearest to in between RHS N82D and 85A.

*Labellum.*—Shape — Three-lobed; the shape of the lateral lobes is obovate, and the aspect is involute; the shape of the central lobe is broad oblong, and the aspect is slightly revolute. Length — Central lobe — Approximately 1.8 cm. Lateral lobes — Approximately 0.8 cm. Width — Central lobe — Approximately 1.4 cm at the base; 1.0 at the apex. Lateral lobes — Approximately 0.5 cm. Apex — Central lobe — Emarginate. Lateral lobes — Obtuse. Base — Central lobe — Cuneate. Lateral lobes — Cuneate. Margin — Central lobe — Entire; lightly undulated. Lateral lobes — Entire; not undulated. Texture and luster of upper surface — Central lobe — Glabrous, velvety, and moderately glossy. Lateral lobes — Glabrous, velvety, and moderately glossy. Texture and luster of lower surface — Central lobe — Glabrous, velvety, and slightly glossy with a glossy apex. Lateral lobes — Glabrous, velvety, and matte. Color when opening, upper surface — Central lobe — Purple, nearest to RHS 79A, and suffused with darker purple to greyed-purple towards the apex, nearest to in between RHS 79A and N186B. Lateral lobes — Purple, nearest to N77A, and radially striped yellow-green, nearest to RHS 154D. Color when opening, lower surface — Central lobe — Purple, nearest to RHS 79A, and suffused with greyed-purple towards the apex, nearest to RHS N186B. Lateral lobes — Purple, nearest to N77C, and radially striped and suffused with greyed-green, nearest to RHS 197C. Color when fully opened, upper surface — Central lobe — Purple, nearest to RHS 79A, and suffused with darker purple to greyed-purple towards the apex, nearest to in between RHS 79A and N186B. Lateral lobes — Purple, nearest to N77A, and radially striped yellow-green, nearest to RHS 154C. Color when fully opened, lower surface — Central lobe — Purple, nearest to RHS 79A, and suffused with greyed-purple towards the apex, nearest to RHS N186B. Lateral lobes — Purple, nearest to N77C, and radially striped and suffused with greyed-green, nearest to RHS 197C. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities.*—Dimensions — 1.6 cm long and 0.6 cm wide, on average. Color — Purple, nearest to RHS 79A, and suffused with darker purple to greyed-purple towards the apex, nearest to in between RHS 79A and N186B.

*Spurs.*—Quantity — Average of 1. Length — Approximately 0.4 cm. Diameter — Approximately 0.3 cm. Vertical height — Approximately 0.6 cm, at the base. Shape — Short triangular; flattened. Apex — Bluntly acute. Base — Broad cuneate. Pubescence, texture and luster — Glabrous, smooth, and matte. Color — Greyed-purple, nearest to RHS N187B, and radially striped and suffused with greyed-purple, nearest to RHS 197C.

*Sepals.*—Quantity — Average of 3 unfused sepals. Arrangement — One dorsal sepal and two lateral sepals. Length — Dorsal sepal — Approximately 5.7 cm. Lateral sepals — Approximately 5.9 cm. Width — Dorsal sepal — Approximately 5.3 cm. Lateral sepals — Approximately 6.3 cm. Shape — Dorsal sepal — Broad ovate. Lateral sepals — Reniform. Apex — Dorsal sepal — Obtuse. Lateral sepals — Obtuse. Base — Dorsal sepal — Cuneate. Lateral sepals — Cuneate. Margin — Dorsal sepal — Entire; no undulation to lightly undulated. Lateral sepals — Entire; no undulation to lightly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — In between purple-violet and violet, between N82D and 85A, and fading purple towards the base, nearest to RHS 76C; base is greyed-purple, nearest to RHS N186B; sepal is finely dotted and blotched with purple, nearest to RHS N79A. Lateral sepals — A mixture of yellow-green and purple, nearest to RHS 150C, 76C and 76D; sepal is heavily dotted and blotched purple, nearest to RHS N77A and 79A. Color when opening, lower surface — Dorsal sepal — Purple-violet, nearest to RHS N82D. Lateral sepals — Yellow-green, nearest to RHS 145B, with purple reticulate veining, nearest to RHS N77C. Color when fully opened, upper surface — Dorsal sepal — In between purple-violet and violet, between N82D and 85A; base is greyed-purple, nearest to RHS N186B; sepal is finely dotted and blotched with purple, nearest to RHS N79A. Lateral sepals — A mixture of violet, in between RHS 85A and 85B, and greyed-purple, nearest to RHS 197B and 197C; sepal is very heavily blotched and veined purple to greyed-purple, nearest to in between RHS 79A and N186B. Color when fully opened, lower surface — Dorsal sepal — In between purple-violet to violet, between RHS N82D and 85A. Lateral sepals — Violet, nearest to RHS 85A, and heavily suffused with greyed-green, nearest to RHS 197C. Fading, upper surface — Not fading. Fading, lower surface — Not fading. Venation — Densely reticulate. Venation color, fully opened, upper surface — Dorsal sepal — In between purple-violet and violet, between N82D and 85A; base is greyed-purple, nearest to RHS N186B; sepal is finely dotted and blotched with purple, nearest to RHS N79A. Lateral sepals — In between purple and greyed-purple, between RHS 79A and N186B. Venation color, fully opened, lower surface — Dorsal sepal — Only the main vein is visible; main vein is violet, nearest to RHS 85A. Lateral sepals — Only the main vein is visible; main vein is violet, nearest to RHS 85A.

*Pedicels.*—Length — Approximately 6.3 cm. Diameter — Approximately 0.45 cm. Angle — Approximately 80 degree angle to peduncle axis. Strength — Moderate. Texture — Glabrous, axially angled with 5 "ribs", axially twisted (due to resupination). Luster — Glossy. Color — Purple-violet, nearest to RHS N80A, and fading to purple towards the proximal end, nearest to RHS N77B.

*Bract.*—Quantity — One bract present at the base of each pedicel. Shape — Broad oblong; folded around the base of each pedicel. Dimensions — Average of 1.9 cm long and 1.2 cm wide. Apex — Broad obtuse. Base — Broad cuneate. Margins — Entire. Color, inner surface — Yellow-green, nearest to RHS 150B. Color, outer surface — Yellow-green, nearest to RHS 150B.

Reproductive organs:

*Column.*—Length — Approximately 0.6 cm. Diameter — Approximately 0.8 cm. Color — Yellow-green, nearest to RHS 154D; base is purple-violet, nearest to RHS N80A.

*Ovary.*—Position — Inferior. Diameter — Approximately 0.2 cm. Color — Yellow-green, nearest to RHS 150D.

*Pollinia color.*—Yellow-orange, nearest to RHS 17B.

Seed and fruit: No fruit and seed production has been detected to date.

COMPARISON WITH THE PARENT PLANTS

Plants of the new cultivar 'SPCDW1702' differ from the *Vanda* seed parent, 'K1BL' (not patented), by the characteristics described in Table 1.

TABLE 1

| Characteristic | 'SPCDW1702' | 'K1BL' |
|---|---|---|
| Plant size. | Smaller than 'K1BL'. | Larger than 'SPCDW1702'. |
| Flowering habit. | More freely flowering. | Less freely flowering. |
| Flower size. | Larger than 'K1BL'. | Smaller than 'SPCDW1702'. |

TABLE 1-continued

| | | |
|---|---|---|
| General coloration of the petals and sepals (excluding the overlaid color pattern) when fully opened. | Appearing as bicolored, with the upper half of the flower generally colored violet, and the lower half dark purple. | Violet-blue; not appearing as bicolored. |

Plants of the new cultivar 'SPCDW1702' differ from the *Vanda* pollen parent, *Vanda* 'V152N1' (not patented), by the characteristics described in Table 2.

TABLE 2

| Characteristic | 'SPCDW1702' | 'V152N1' |
|---|---|---|
| Foliage length. | Shorter than 'V152N1'. | Longer than 'SPCDW1702'. |
| Flower size. | Larger than 'V152N1'. | Smaller than 'SPCDW1702'. |
| Number of flowers per inflorescence. | Fewer flowers. | More flowers. |
| General coloration of the petals and sepals (excluding the overlaid color pattern) when fully opened. | Appearing as bicolored, with the upper half of the flower generally colored violet, and the lower half dark purple. | Appearing as bicolored; a combination of pink and reddish brown. |

COMPARISON WITH THE MOST SIMILAR *VANDA* CULTIVARS KNOWN TO THE INVENTOR

Plants of the new cultivar 'SPCDW1702' are similar to the cultivar, *Vanda* 'SPCDW1102' (European Community Plant Variety Rights grant number 33691). A comparison of 'SPCDW1702' with *Vanda 'SPCDW*1102' is described in Table 3.

TABLE 3

| Characteristic | 'SPCDW1702' | 'SPCDW1102' |
|---|---|---|
| Foliage length. | Shorter than 'SPCDW1102'. | Longer than SPCDW1702'. |
| General coloration of the lateral sepals (excluding the overlaid color pattern) when fully opened. | Violet. | Dark red-purple. |
| General coloration of the petals (including the overlaid color pattern) when fully opened. | Violet and dotted dark purple. | Light purple with larger red-purple dots. |

Plants of the new cultivar 'SPCDW1702' are also similar to the cultivar, *Vanda* 'SPCDW1106' (European Community Plant Variety Rights grant number 33693). A comparison of 'SPCDW1702' with *Vanda* 'SPCDW1106' is described in Table 4.

TABLE 4

| Characteristic | 'SPCDW1702' | 'SPCDW1106' |
|---|---|---|
| Undulation of the petals and sepals. | Not undulated to lightly undulated. | Lightly undulated, more so than 'SPCDW1702'. |
| General coloration of the petals (including the overlaid color pattern) when fully opened. | Violet and dotted dark purple. | Light purple with larger red-purple dots. |
| General coloration of the lateral sepals. | Dark purple. | Dark red-purple. |

That which is claimed is:

1. A new and distinct variety of *Vanda* plant named 'SPCDW1702', substantially as described and illustrated herein.

* * * * *